United States Patent [19]
Asouzu et al.

[11] Patent Number: 6,027,624
[45] Date of Patent: Feb. 22, 2000

[54] AUTOMATED CAPILLARY ELECTROPHORESIS METHOD AND APPARATUS

[75] Inventors: Moore Ugochukwu Asouzu, Montgomery, Ala.; Shawn Anderson, Kissimmee, Fla.

[73] Assignee: Troy State University, Troy, Ala.

[21] Appl. No.: 08/852,828

[22] Filed: May 7, 1997

[51] Int. Cl.$^7$ .................................................... G01N 27/26
[52] U.S. Cl. ........................... 204/452; 204/602; 204/603
[58] Field of Search .................................... 204/451, 452, 204/461, 600, 601, 602, 603

[56] References Cited

U.S. PATENT DOCUMENTS 5,599,433  2/1997  Keo et al. ................................ 204/451

OTHER PUBLICATIONS

Altria, K.D. and Simpson, C.F., High Voltage Capillary Zone Electrophoresis: Operating Parameters Effects On Electroendosmotic Flows And Electrophoretic Mobilities, *Chromatographia*, vol. 24, 1987, pp. 527–32.

Bondoux, G., Jandik, P., and Jones, W.R., New approach to the analysis of low levels of anions in water, *Journal of Chromatography*, vol. 602, 1992, pp. 79–88.

Bruin, G.J.M., van Asten, A.C., et al, Theoretical and experimental aspects of indirect detection in capillary electrophoresis, *Journal of Chromatography*, vol. 608, 1992, pp. 97–107.

Brumley, W. C., Qualitative analysis of environmental samples for aromatic sulfonic acids by high–performance capillary electrophoresis, *Journal of Chromatography*, vol.603, 1992, pp. 267–272.

Buchberger, W. and Haddad, P.R., Effects of carrier electrolyte composition on separation selectivity in capillary zone electrophoresis of low–molecular–mass anions, *Journal of Chromatography*, vol. 608, 1992, pp. 59–64.

Hjertén, S., Elenbring, K., et al, Carrier–Free Zone Electrophoresis, Displacement Electrophoresis and Isoelectric Focusing in a High–Performance Electrophoresis Apparatus, *Journal of Chromatography*, vol. 403, 1987, pp. 47–61.

Jackson, P.E. and Haddad, P.R., Capillary electrophoresis of inorganic ions and low–molecular–mass ionic solutes, *Trends in Analytical Chemistry*, vol. 12, No. 6, 1993, pp. 231–238.

(List continued on next page.)

*Primary Examiner*—David A. Redding
*Attorney, Agent, or Firm*—Alston & Bird LLP

[57] ABSTRACT

The automated capillary electrophoresis method and apparatus analyzes a sample in real time or near real time in order to identify the presence of a number of different ions as well as other sample parameters, such as the relative concentrations of each ion identified in the sample. By performing capillary electrophoresis in an automated fashion, the automated capillary electrophoresis method and apparatus may be configured to monitor a manufacturing process online with little, if any, input from the system operator. The automated capillary electrophoresis method and apparatus also provides a base line such that the analysis results can be compared and can be more meaningfully interrupted. The automated capillary electrophoresis method and apparatus initially performs capillary electrophoresis upon a sample containing at least one ion to obtain data over time which relates to a predetermined property of the sample, such as the degree of transparency of at least a portion of the sample. This time dependent data is then automatically processed to determine one or more sample parameters. In this regard, the time dependent data is automatically processed to identify at least one peak within the data by determining those portions of the data which exceed a predetermined threshold. By separately determining the area under respective ones of the peaks, the capillary electrophoresis method and apparatus can automatically determine sample parameters, including the concentrations of the ions corresponding to the respective peaks.

16 Claims, 11 Drawing Sheets

OTHER PUBLICATIONS

Jackson, P.E. and Haddad, P.R., The Occurrence and Origin of System Peaks in Non–Suppressed Ion Chromatography of Inorganic Anions with Indirect Ultraviolet Absorption Detection, *Journal of Chromatography,* vol. 346, 1985, pp. 125–137.

Jandik, P. and Jones, W.R., Optimization of detection sensitivity in the capillary electrophoresis of inorganic anions, *Journal of Chromatography,* vol. 546, 1991, pp. 431–443.

Jones, W.R. and Jandik, P., Various approaches to analysis of difficult sample matrices of anions using capillary ion electrophoresis, *Journal of Chromatography,* vol. 608, 1992, pp. 385–393.

Jones, W.R. and Jandik, P., New Methods for chromatographic separations of anions, *American Laboratory,* Jun. 1990, pp. 51–64.

Jones, W.R. and Jandik, P., Controlled changes of selectivity in the separation of ions by capillary electrophoresis, *Journal of Chromatography,* vol. 546, 1991, pp. 445–458.

Morin, Ph., Villard, F., Dreux, M., Short Communication: Borate complexation of flavonoid–O–glycosides in capillary electrophoresis, *Journal of Chromatography,* vol. 628, 1993, pp. 161–169.

Nair, J.B. and Izzo, C.G., Anion screening for drugs and intermediates by capillary ion electrophoresis, *Journal of Chromatography,* vol. 640, 1993, pp. 445–461.

Nielen, M.W.F., Indirect time–resolved luminescence detection in capillary zone electrophoresis, *Journal of Chromatography,* vol. 608, 1992, pp. 85–92.

Romano, J.P. and Krol, Jim, Capillary ion Electrophoresis, An Environmental Method for the Determination of Anions in Water, *Journal of Chromatography,* vol. 640, 1993, pp. 403–412.

Salomon, D.R. and Romano, Joe, Applications of Capillary Ion Electrophoresis in the Pulp and Paper Industry, *Journal of Chromatography,* vol. 602, 1992, pp. 219–225.

Weston, A., Brown, P.R., et al, Effect of electrolyte composition on the separation of inorganic metal cations by capillary ion electrophoresis, *Journal of Chromatography,* vol. 602, 1992, pp. 249–256.

AUTOMATED CAPILLARY ELECTROPHORESIS METHOD AND APPARATUS

FIELD OF THE INVENTION

The present invention relates generally to capillary electrophoresis methods and apparatus and, more particularly, to automated capillary electrophoresis methods and apparatus for identifying and analyzing ions.

BACKGROUND OF THE INVENTION

It is important in many applications to identify ions within a sample. For example, a manufacturing process may be monitored by identifying the ions present at various stages of the manufacturing process and by determining the concentration of the ions. If necessary, the manufacturing process can then be adjusted to bring the concentration of the ions into the proper balance.

One industry in which ion concentration is closely monitored is the pulp and paper industry. During the chemical pulping of wood to obtain cellulose for papermaking, for example, inorganic chemicals are mixed with wood chips to separate lignin from the wood fibers. The lignin is then removed by cooking the wood chips in an aqueous solution of sodium hydroxide (NaOH) and white liquor. The white liquor includes $Na_2S$ and smaller amounts of $Na_2CO_3$, $Na_2SO_4$, $Na_2S_2O_3$ and $Na_2SO_3$. Once cooked, the spent liquor, i.e., black liquor containing both organic and inorganic anions, is concentrated and burned in a recovery furnace to obtain a smelt of $Na_2CO_3$ and $Na_2S$. The molten sodium salts are dissolved to form green liquor which is then reacted with calcium hydroxide ($Ca(OH)_2$) to regenerate the white liquor.

In addition to monitoring the temperature/time profile of chip digestion, the liquor composition must be carefully controlled during all phases of the kraft pulping process in order to properly separate lignin from the wood fibers. In this regard, the composition of the liquors obtained from the combustion of the black liquor and the regeneration of the white liquor will reveal whether targeted performance schedules have been met and, in turn, will determine the quality of the resulting cellulose. The liquors of the kraft pulping process include a number of anions, namely, hydroxide, sulfide, carbonate, sulfate, chloride, thiosulfate and sulfite anions, which are critical to the quality of the pulping. As a result, a significant portion of mill time is consumed by the monitoring of the concentrations of these anions to determine process performance. Historically, this anion analysis has been performed off-line by various gravimetric and titrimetric procedures. See D. R. Salomon et al. "Applications of Capillary Ion Electrophoresis in the Pulp and Paper Industry", *Journal of Chromatography*, Vol. 602, pp. 219–25 (1992).

In addition to the gravimetric and titrimetric procedures utilized in the kraft pulping industry, a number of other ion analysis methods have been developed. For example, a number of electrophoresis methods have been developed for identifying and analyzing ions. Electrophoresis involves the migration of electrically charged particles, such as ions, in solution or suspension in the presence of an applied electric field. For a given set of solution conditions, the velocity with which an ion moves divided by the magnitude of an electric field is a characteristic number called the electrophoretic mobility. The electrophoretic mobility is directly proportional to the magnitude of the charge on the particle and is inversely proportional to the size of the particle. By separating ions from each other in the electric field on the basis of charge or size, the different ions can be identified and measured.

Capillary electrophoresis (CE) and, more particularly, capillary zone electrophoresis (CZE) are variations of standard electrophoresis techniques. In capillary zone electrophoresis, a capillary of a nonconducting material, such as fused silica, is filled with a buffer solution and is immersed in buffer reservoirs at both ends. The sample to be analyzed, i.e., the analyte, is applied to the head of the capillary in a narrow band having a width much less than the length of the capillary tube and at concentrations too low to affect the conductivity of the buffer solution. By applying a relatively large electric field across the length of the capillary tube, such as 10,000–30,000 volts, the various species within the sample separate into zones based upon their respective electrophoretic mobilities and migrate through the capillary tube. The moving analyte bands or zones are detected based upon ultraviolet light absorption or fluorescence emission, or an electrochemical property of the moving bands. In either instance, the capillary zone electrophoresis technique obtains a value relating the measured property to the different analyte zones. The measured property of each analyte zone defines, at least in part, various parameters relating to the respective ion, such as the concentration of the respective ion.

Conventional capillary electrophoresis techniques include a detector such as an ultraviolet absorption detector for both illuminating the moving analyte sample and for detecting the amount of light absorbed by the moving analyte zones. Based upon the data collected by the ultraviolet absorption detector, a measure of the degree of transparency of the sample and, in turn, a measure of the concentration of the respective ions is obtained. Typically, however, the data collected by the ultraviolet absorption detector must be analyzed by the system operator in order to determine the presence and/or the concentration of the various ions. As will be apparent to those skilled in the art, the data analysis can be quite time consuming and labor intensive. It is also relatively difficult to compare the capillary electrophoresis analysis results of samples obtained at two different times since there is no common base line.

Conventional instruments for performing capillary electrophoresis typically include several stand-alone hardware modules that must be properly interconnected in order to receive the data collected by the detector and to generate corresponding electropherograms. In addition to the relatively large cost of the hardware modules and the difficulties encountered in properly interconnecting the hardware modules, the stand-alone hardware modules of conventional instruments for performing capillary electrophoresis are generally configured to receive data collected by one specific type of detector, such as an absorption detector, a fluorescence detector or an electrochemical detector. As such, the stand-alone hardware modules of conventional instruments for performing capillary electrophoresis cannot typically receive and process data collected by detectors other than the one specific type of detector for which they are designed.

As with conventional gravimetric and titrimetric methods, capillary electrophoresis and, in particular, capillary zone electrophoresis is typically performed off-line. In this respect, a sample is obtained from one or more stages of a manufacturing process. These samples are then analyzed by capillary electrophoresis as the manufacturing process continues. Based upon the results of the capillary electrophoresis analysis, such as based upon the presence and/or the concentration of the various ions within the sample, the manufacturing process can be adjusted to bring the concentrations of the respective ions within a desired range. The time delays inherent in this off-line analysis, including the time required by the system operator to analyze the data, can create problems if the analysis indicates that the manufacturing process was operating outside of specifications. In this event, the resulting product produced during the time required to conduct the capillary electrophoresis analysis may have to be discarded or reprocessed.

SUMMARY OF THE INVENTION

The automated capillary electrophoresis method and apparatus of the present invention can analyze a sample in real time or near real time. For example, the automated capillary electrophoresis method can identify the presence of a number of different ions as well as other sample parameters, such as the relative concentrations of each ion identified in the sample. By performing capillary electrophoresis in an automated fashion, the method and apparatus of the present invention is capable of monitoring a manufacturing process on-line with little, if any, input from the system operator. The automated capillary electrophoresis method and apparatus also provides a base line such that the analysis results can be compared and can be more meaningfully interrupted.

The automated capillary electrophoresis method and apparatus initially performs capillary electrophoresis upon a sample containing at least one ion to obtain data over time which relates to a predetermined property of the sample, such as the degree of transparency of at least a portion of the sample to ultraviolet light. The automated capillary electrophoresis apparatus includes a signal processor for automatically processing the data to determine one or more sample parameters. The signal processor of one embodiment can include a computer program product having a computer-readable storage medium including computer readable program code means for automatically processing the data to determine one or more sample parameters. Since the signal processor can be implemented in software, the automated capillary electrophoresis method and apparatus may be significantly less expensive than conventional instruments for performing capillary electrophoresis that include several stand-alone hardware modules.

Regardless of the implementation, the signal processor automatically identifies at least one peak within the data by determining those portions of the data which exceed a predetermined threshold. Each peak within the data corresponds to a respective ion. By separately determining the area under respective ones of the peaks, the signal processor can automatically determine sample parameters, including parameters associated with the ions corresponding to the respective peaks. For example, the automated capillary electrophoresis method and apparatus can automatically determine the concentration of a respective ion based upon the area under the peak which corresponds to the respective ion. Alternatively, the automated capillary electrophoresis method and apparatus can automatically determine one or more sample parameters which have been selected in advance by the system operator and which at least partially define the sample. Once the concentration or other sample parameters have been determined, the automated capillary electrophoresis method and apparatus can automatically display the selected parameters.

In one advantageous embodiment, the automated capillary electrophoresis method and apparatus is configured to automatically monitor the liquor composition within a kraft process. The automated capillary electrophoresis method and apparatus of this embodiment can therefore automatically determine the concentration of a respective ion selected from a group consisting of chloride ions, thiosulfate ions, hydroxide ions, carbonate ions, sulfate ions, sulfite ions and sulfide ions. The automated capillary electrophoresis method and apparatus of this embodiment can also automatically determine sample parameters, such as percent activity and percent sulfidity, based upon the concentration of the respective ions.

The results obtained by the automated capillary electrophoresis method and apparatus can be further enhanced by analyzing the peaks identified within the data to determine if the data is acceptable. If the data is not acceptable, the automated capillary electrophoresis method and apparatus can again subject the sample to capillary electrophoresis to obtain acceptable data. For example, the automated capillary electrophoresis method and apparatus can automatically analyze the peaks identified within the data to determine if a peak is skewed and, if so, to determine if the peak is unacceptably skewed. Additionally, the automated capillary electrophoresis method and apparatus of one embodiment subjects the sample to several runs. As such, the corresponding peaks identified within the data obtained during the various runs can be automatically compared. Based upon this comparison, the automated capillary electrophoresis method and apparatus can automatically determine if the data obtained during one or more of the runs is unacceptable.

In order to establish a base line for comparison purposes, the automated capillary electrophoresis method and apparatus not only performs capillary electrophoresis upon the sample, but also preferably performs capillary electrophoresis upon a solution containing both the sample and a standard ion solution. As such, the selected parameter, such as the concentration of a respective ion, can be automatically determined based, in part, upon the area under the peak corresponding to the ion which was identified within the data obtained by the capillary electrophoresis of the sample. However, the selected parameter, such as the concentration of a respective ion, is also automatically determined based, in part, upon the area under the peak corresponding to the ion which was identified within the additional data obtained during capillary electrophoresis of the solution containing both the sample and the standard ion solution. Thus, the results obtained by this embodiment of the automated capillary electrophoresis method and apparatus can be more easily interpreted and can be more readily compared to other test results.

The automated capillary electrophoresis method and apparatus can therefore determine, in a reliable, accurate and timely manner, various sample parameters, such as the concentration of respective ones of the ions within the sample, with little, if any, input from the system operator. Based upon the results provided by the automated capillary electrophoresis method and apparatus, a manufacturing process, such as a kraft process, can be modified or optimized on a real time or near real time basis, thereby avoiding the continued production of products which are not within specifications or are otherwise unacceptable. The automated capillary electrophoresis method and apparatus is also capable of receiving and processing data collected by a variety of different detectors, such as absorption detectors, fluorescence detectors and electrochemical detectors, such that the automated capillary electrophoresis method and apparatus can be employed in a wide range of applications.

DETAILED DESCRIPTION OF THE PREFERRED EMBODIMENTS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
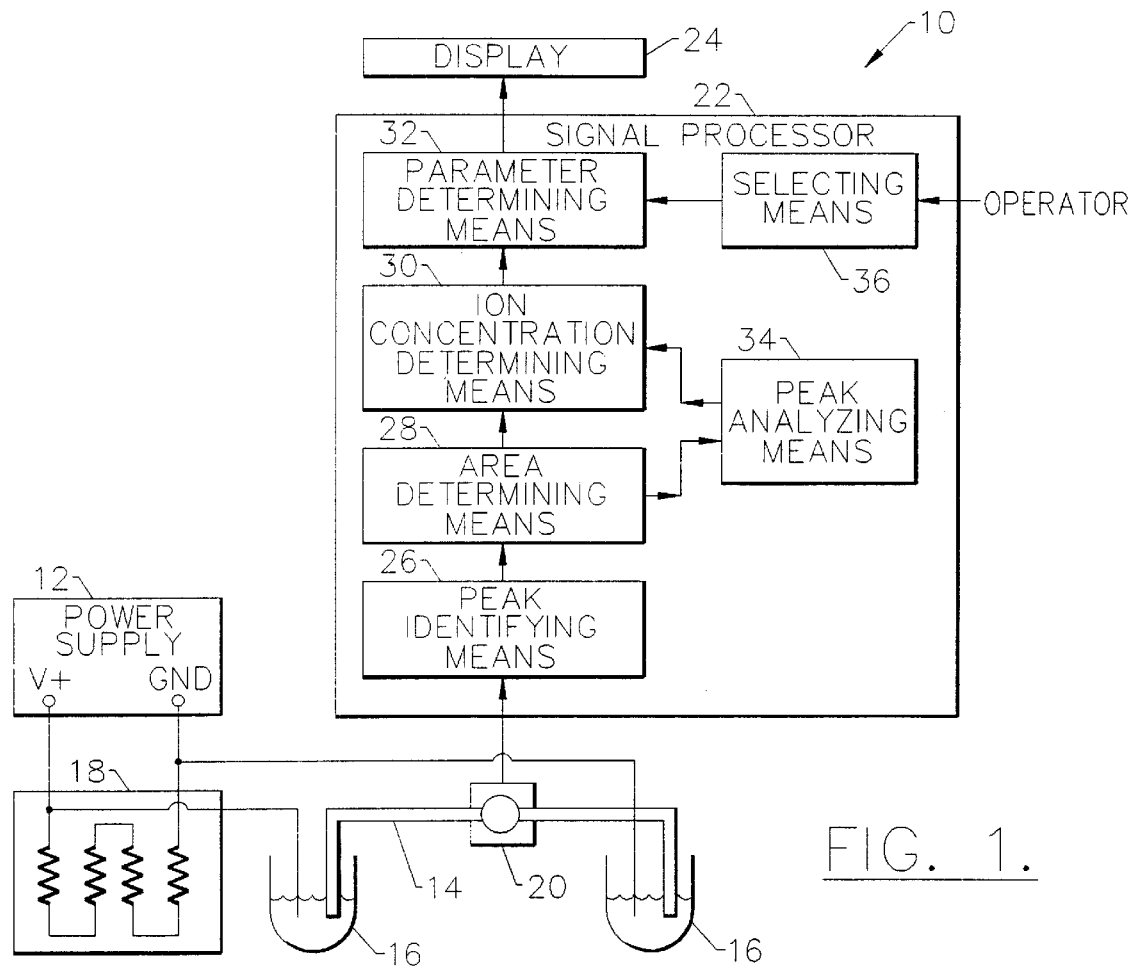
FIG. 1 is a block diagram of an automated capillary electrophoresis apparatus according to one embodiment of the present invention.

Referring now to FIG. 1, an automated capillary electrophoresis apparatus 10 is illustrated. As shown, the apparatus includes a capillary 14 extending between a pair of sample reservoirs 16. The capillary is preferably a polyamide-coated fused-silica capillary. In addition, the sample reservoirs are preferably nalgene containers. However, other types of capillaries and sample reservoirs known to those skilled in the art can be employed without departing from the spirit and scope of the present invention.

As shown in FIG. 1, each sample reservoir 16 is at least partially filled with an electrolyte solution. For example, the electrolyte solution can be a chromate solution. By applying an electric potential across the capillary 14, the electrolyte solution is drawn through the capillary. As shown in FIG. 1, the capillary electrophoresis apparatus 10 includes a power supply 12, such as shielded, dual-polarity, switchable high voltage power supply. In one embodiment, the power supply provides between about 10,000 volts and about 30,000 volts. However, the power supply can provide other power levels without departing from the spirit and scope of the present invention. The capillary electrophoresis apparatus can also include a current sink 18 for reducing the relative current levels.

As explained in more detail below, a sample containing at least one ion is introduced at the head end of the capillary 14 such that the sample is also drawn through the capillary by the electric potential applied across the capillary or by hydrostatic injection at a set height. Due to the different electrophoretic mobilities of the ions within the sample, the sample will typically separate into zones.

The capillary electrophoresis apparatus 10 also includes a detector 20, such as a Spectra 100™ ultraviolet/visible wavelength detector having a deuterium lamp and one or more monochromators for controlling the wavelength of light emitted by the detector. The capillary electrophoresis apparatus can include other types of detectors, such as a photodiode-array detector or an electrochemical detector, if so desired. The detector irradiates the capillary 14 with a light of a predetermined wavelength, such as light having a wavelength of 214 nanometers. For a chromate electrolyte solution, the solution will absorb light having a wavelength of 214 nanometers. However, the sample to be analyzed is also drawn to through the capillary 14 by the electric potential applied across the capillary. The sample will therefore displace at least some of the electrolyte solution. In contrast to the electrolyte solution, the sample is transparent to light of the predetermined wavelength. By detecting the light passing through the capillary, the detector of this embodiment obtains a measure of the transparency of the solution within the capillary and, in turn, a measure of the degree of transparency of the sample. By illuminating the capillary for a period of time and by detecting the light passing through the capillary at different instances in time, the detector of this embodiment obtains a measure of the degree of transparency of each of the different zones into which the sample separates. Although the detector of this embodiment is designed to detect the degree of transparency of the sample, the detector of other embodiments can measure predetermined properties of the sample other than its degree of transparency, such as the fluorescence or other electrochemical properties of the sample.

The automated capillary electrophoresis apparatus 10 also includes a signal processor 22 for automatically processing the data obtained over time by the detector 20. The signal processor processes the data to determine predetermined sample parameters, such as the concentration of respective ions within the sample. The automated capillary electrophoresis apparatus can also include a display 24 for automatically displaying the results of the automated capillary electrophoresis analysis.

The signal processor 22 is typically comprised of a combination of hardware, such as one or more controllers or processors, and software, such as a computer program product. In one advantageous embodiment, the signal processor comprises a computer program product which includes a computer-readable storage medium having computer-readable program code means, such as a series of computer instructions preferably written in a graphical programming language such as the LabView™ Graphical Environment, embodied in the computer-readable storage medium for automatically processing the data collected over time by the detector 20 in order to determine selected parameters which at least partially define the sample, such as the concentration of one or more respective ions within the sample.

Since the signal processor 22 of this advantageous embodiment is a computer program product, the signal processor can be significantly less expensive than conventional instruments for performing capillary electrophoresis that include several stand-alone hardware modules. In addition, the signal processor is capable of receiving and processing data collected by a variety of different detectors, such as absorption detectors, fluorescence detectors and electrochemical detectors, such that the automated capillary electrophoresis method and apparatus 10 can be employed in a wide range of applications.

In this regard, FIGS. 1 and 2A–2C are block diagram, flowchart and control flow illustrations of methods, systems and program products according to the invention. It will be understood that each block or step of the block diagram, flowchart and control flow illustrations, and combinations of blocks in the block diagram, flowchart and control flow illustrations, can be implemented by computer program instructions. These computer program instructions may be loaded onto a computer or other programmable apparatus to produce a machine, such that the instructions which execute on the computer or other programmable apparatus create means for implementing the functions specified in the block diagram, flowchart or control flow block(s) or step(s). These computer program instructions may also be stored in a computer-readable memory that can direct a computer or other programmable apparatus to function in a particular manner, such that the instructions stored in the computer-readable memory produce an article of manufacture including instruction means which implement the function specified in the block diagram, flowchart or control flow block(s) or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the block diagram, flowchart or control flow block(s) or step(s).

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagram, flowchart or control flow illustrations, and combinations of blocks or steps in the block diagram, flowchart or control flow illustrations, can be implemented by special purpose hardware-based computer systems which perform the specified functions or steps, or combinations of special purpose hardware and computer instructions.Many modifications and other embodiments of the invention will come to mind to one skilled in the art to which this invention pertains having the benefit of the teachings presented in the foregoing descriptions and the associated drawings.

Figure 2A:
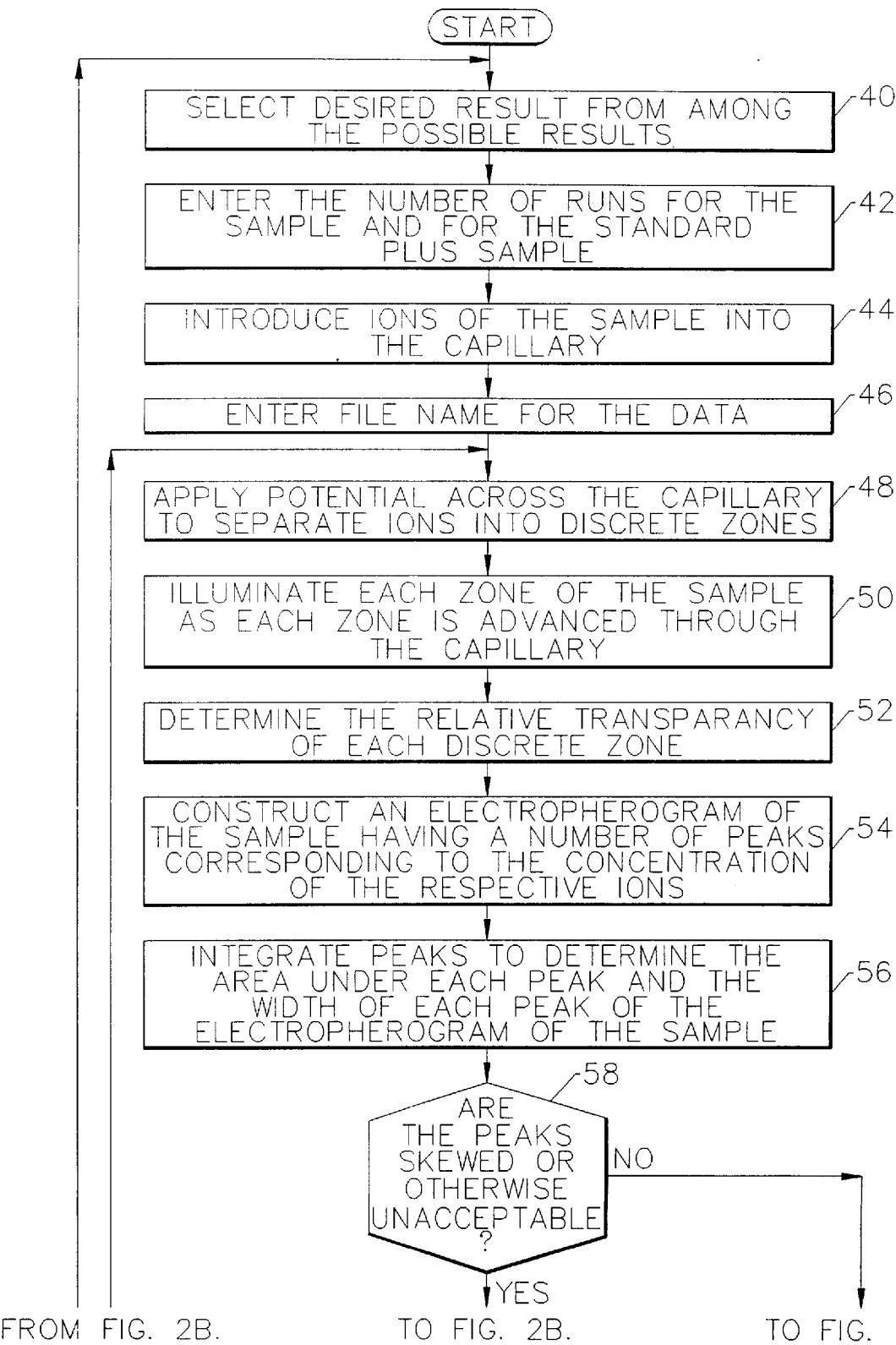
FIGS. 2A–2C are flow charts illustrating the operations performed by the automated capillary electrophoresis method and apparatus according to one embodiment of the present invention.
Figure 2B:
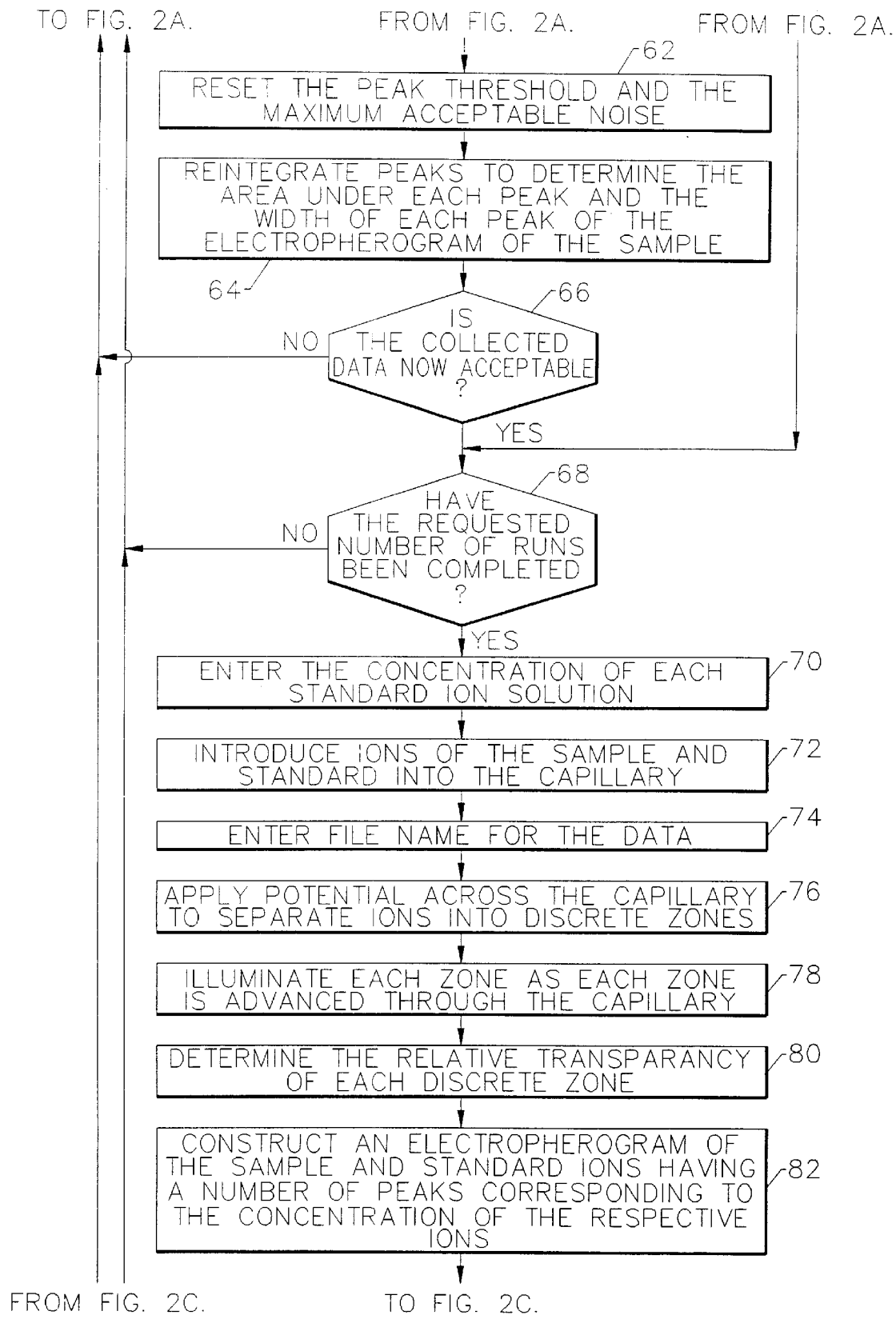
Figure 2C:
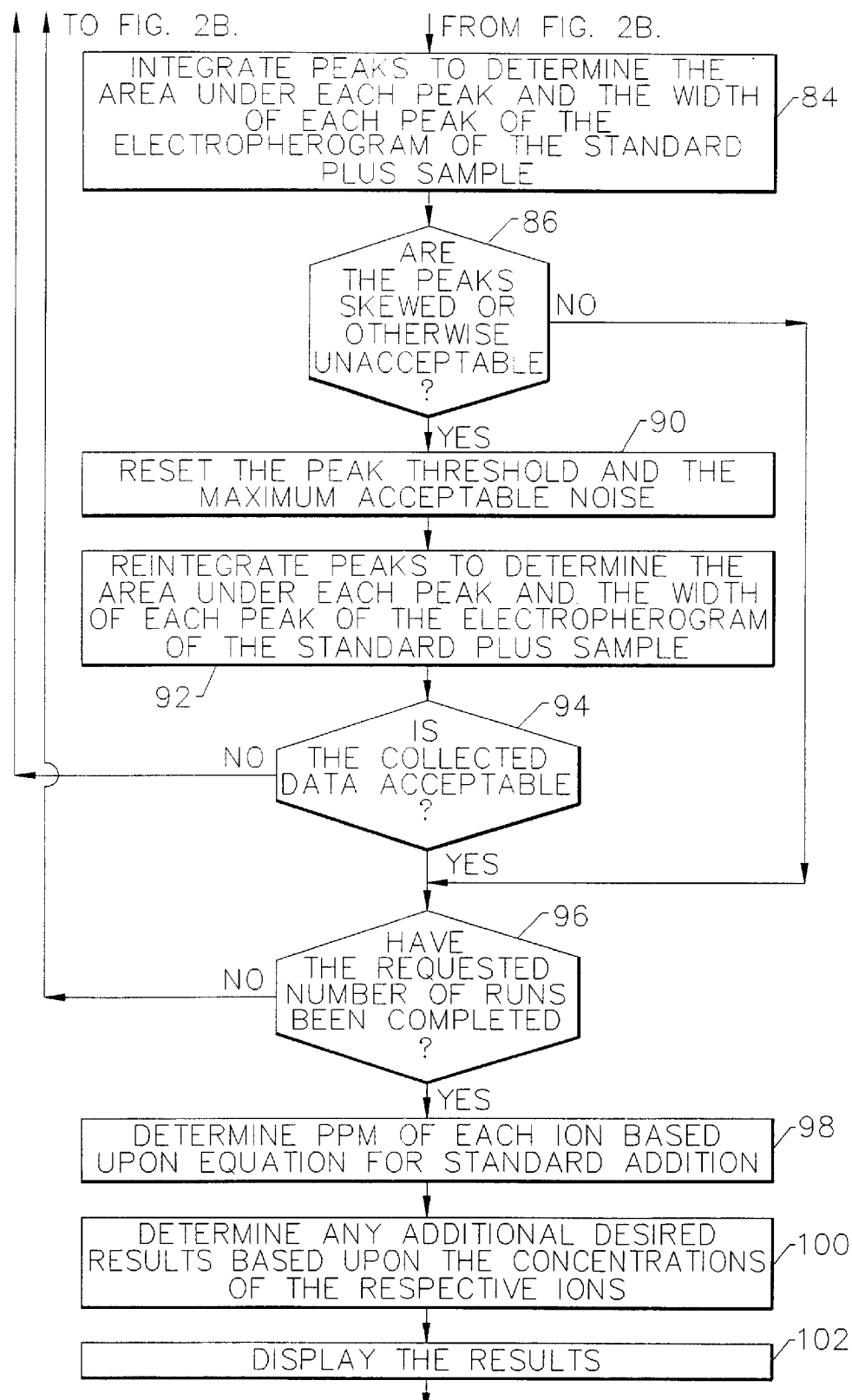

Referring now to FIGS. 2A–2C, a flow chart illustrating the operations performed by the automated capillary electrophoresis method and apparatus 10 is shown. As set forth in block 40, the system operator can initially select one or more parameters of interest which at least partially define the sample or respective ions within that sample. In this regard, the signal processor 22 preferably includes selecting means 36 which provides a listing of all parameters which can be determined by the automated capillary electrophoresis method and apparatus and which serves as an interface with the system operator. Alternatively, the automated capillary electrophoresis method and apparatus can be configured, in advance, to automatically determine one or more predefined parameters such that the system operator need not select the desired parameters prior to operation of the automated capillary electrophoresis method and apparatus.

As described below, the automated capillary electrophoresis method and apparatus 10 can be designed to automatically monitor the liquor composition during a kraft paper process. Due to the nature of a kraft paper process, the percent activity and percent sulfidity of the liquor composition are important parameters. Thus, the operator of an automated capillary electrophoresis method and apparatus which has been adapted to automatically monitor the liquor composition during a kraft paper process would typically select percent activity and percent sulfidity as parameters to be monitored. In other applications, however, the system operator can select other parameters of interest from among the available parameters.

While the automated capillary electrophoresis apparatus 10 need only analyze the sample once to obtain a measure of the selected parameter, the automated capillary electrophoresis apparatus can more accurately determine the selected parameter by analyzing the sample several times and by averaging the results. As shown in block 42, the system operator can therefore also identify the number of times which a sample will be analyzed by entering the number of runs or iterations to be performed on each sample. Typically, the automated capillary electrophoresis method and apparatus produces the most accurate results by separately analyzing the sample at least 4 or 5 times.

Thereafter, the sample is introduced to the sample reservoir 16 at the head end of the capillary 14. See block 44. The sample typically includes one or more ions which will be identified and analyzed by the automated capillary electrophoresis method and apparatus 10. In order to track the results, the system operator is also generally prompted to enter a file name for the data which will be collected as shown in block 46.

As shown in blocks 48 and 50, capillary electrophoresis is then performed upon the sample by applying an electric potential across the capillary 14 to separate the ions into discrete zones based upon the electrophoretic mobility of the respective ions. As each zone is drawn through the capillary, the detector 20 illuminates each zone of the sample with light of a predetermined wavelength, such as 214 nanometers, and detects the light passing through the capillary. The detector of this embodiment therefore obtains a measure of the light passing through the capillary at different instances in time which, in turn, relates to the degree of transparency of the sample and, more particularly, to the degree of transparency of each zone into which the sample separates. See block 52. As described above, however, the detector can obtain data relating to predetermined properties of the sample other than the degree of transparency without departing from the spirit and scope of the present invention.

Based upon the data collected by the detector 20 over time, the automated capillary electrophoresis method and apparatus 10 and, more particularly, the signal processor 22 constructs an electropherogram representative of the sample. The electropherogram has a number of peaks corresponding to the concentration of the respective ions within the sample. See block 54. As shown in FIGS. 4A–4E, an electropherogram depicts the output voltage or absorbance of the detector over time. The output voltage of the detector of this embodiment corresponds directly to the intensity of the light passing through the capillary 14 and, in turn, to the degree of transparency of the solution within the capillary. Due to the differences in electrophoretic mobilities of the respective ions, the sample typically separates into discrete zones having different degrees of transparency which move past the detector at different times. Thus, the output voltage of the detector generally varies over time as the different zones move past the detector and are illuminated. For example, the various peaks of the electropherograms illustrated in FIGS. 4A–4E correspond to respective ions which have been separated into discrete zones by the electric potential applied across the capillary.

Figure 4A:
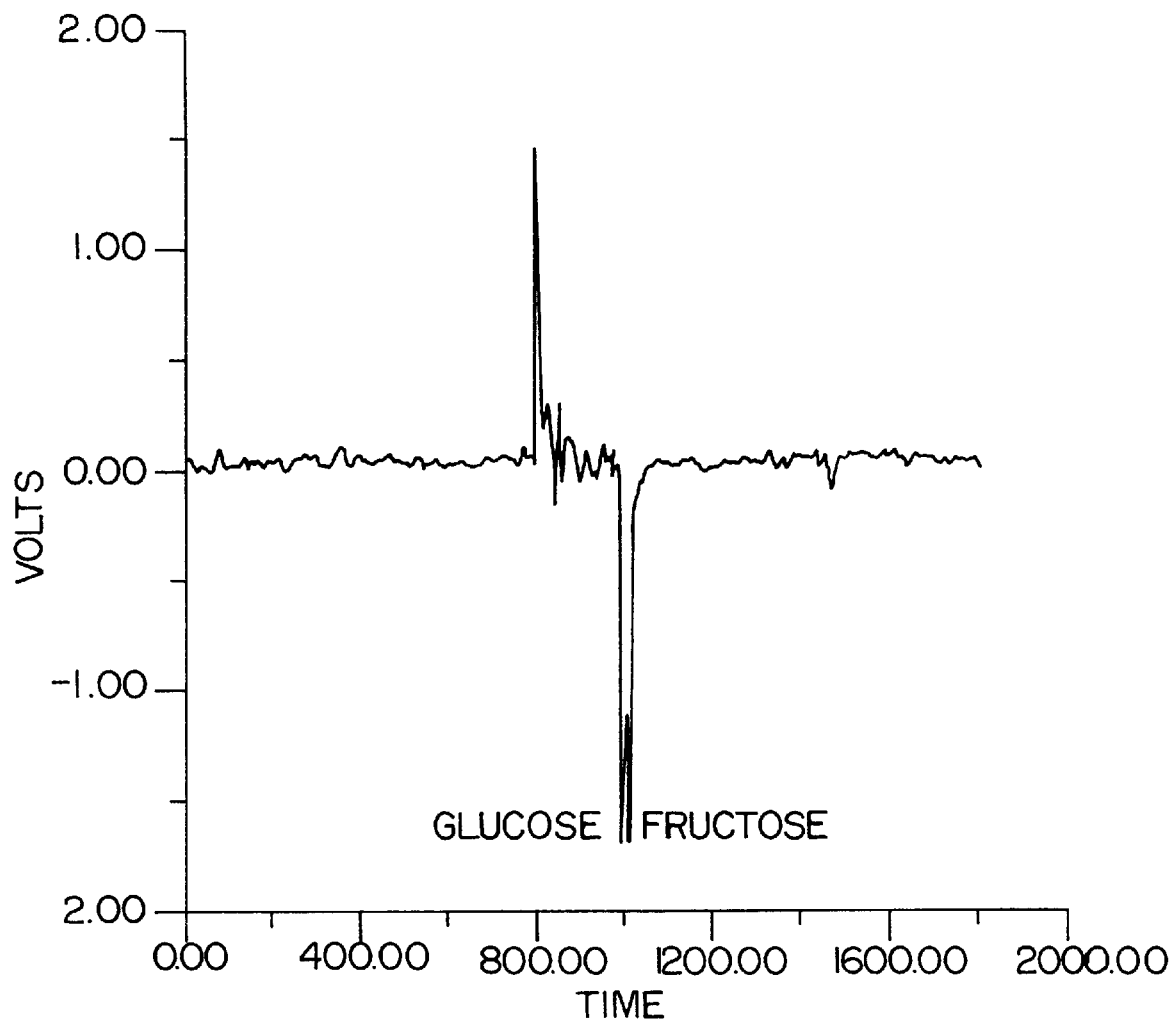
FIGS. 4A–4E are electropherograms for a variety of samples containing different respective ions, such as a Coca-Cola® soft drink, a Diet Coke® soft drink, green liquor, black liquor and white liquor, respectfully.
Figure 4B:
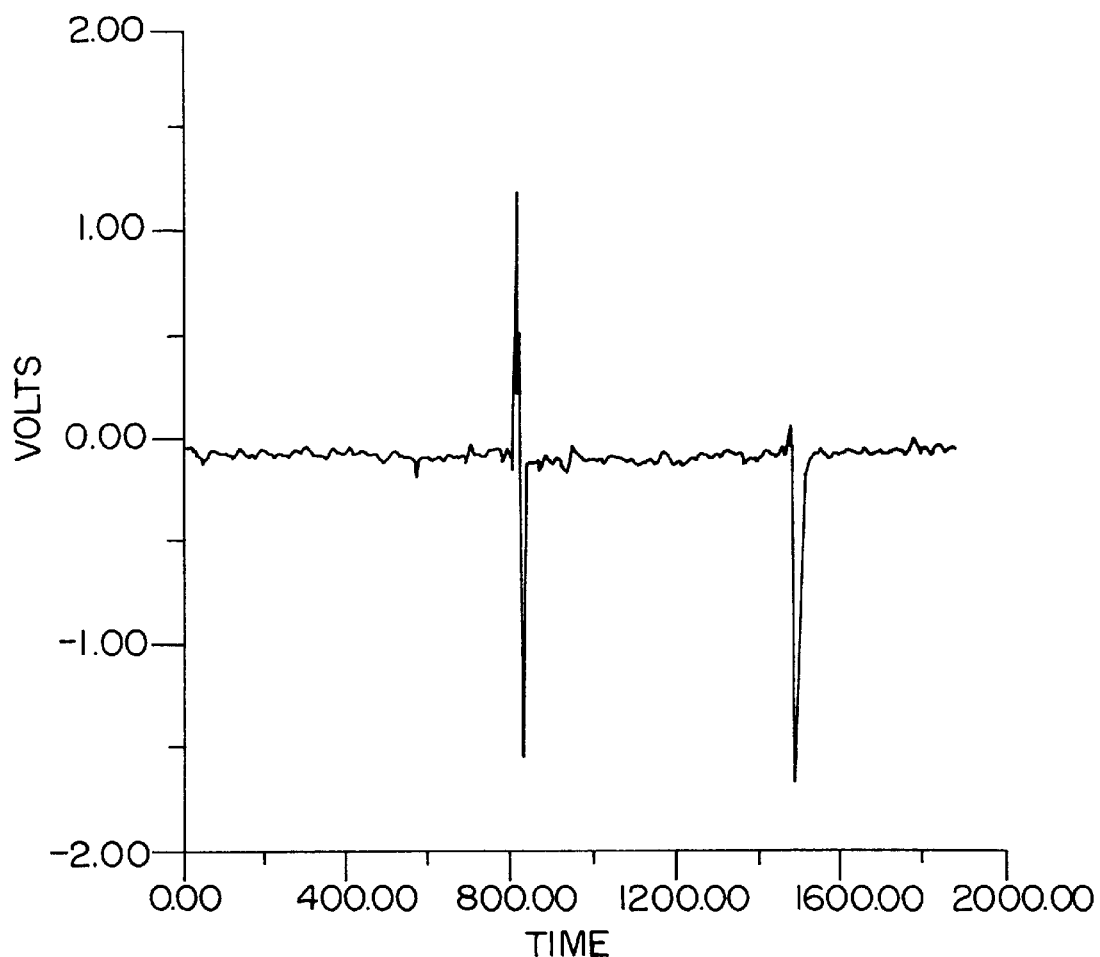

The automated capillary electrophoresis method and apparatus 10 can analyze a wide variety of solutions. In this regard, FIG. 4A illustrates an electropherogram constructed based upon data collected by the automated capillary electrophoresis method and apparatus during an analysis of a Coca-Cola® soft drink. Likewise, FIG. 4B is an electropherogram constructed following an analysis of a Diet Coke® soft drink. By way of example, the automated capillary electrophoresis method and apparatus will be described below in conjunction with the automated monitoring of the liquor composition during a kraft paper process. However, the automated capillary electrophoresis method and apparatus can be employed to analyze a variety of other solutions in addition to cola syrup and liquor compositions including biological samples, such as amine sugars in chitin and a mixture of phenols, without departing from the spirit and scope of the present invention.

Figure 5A:
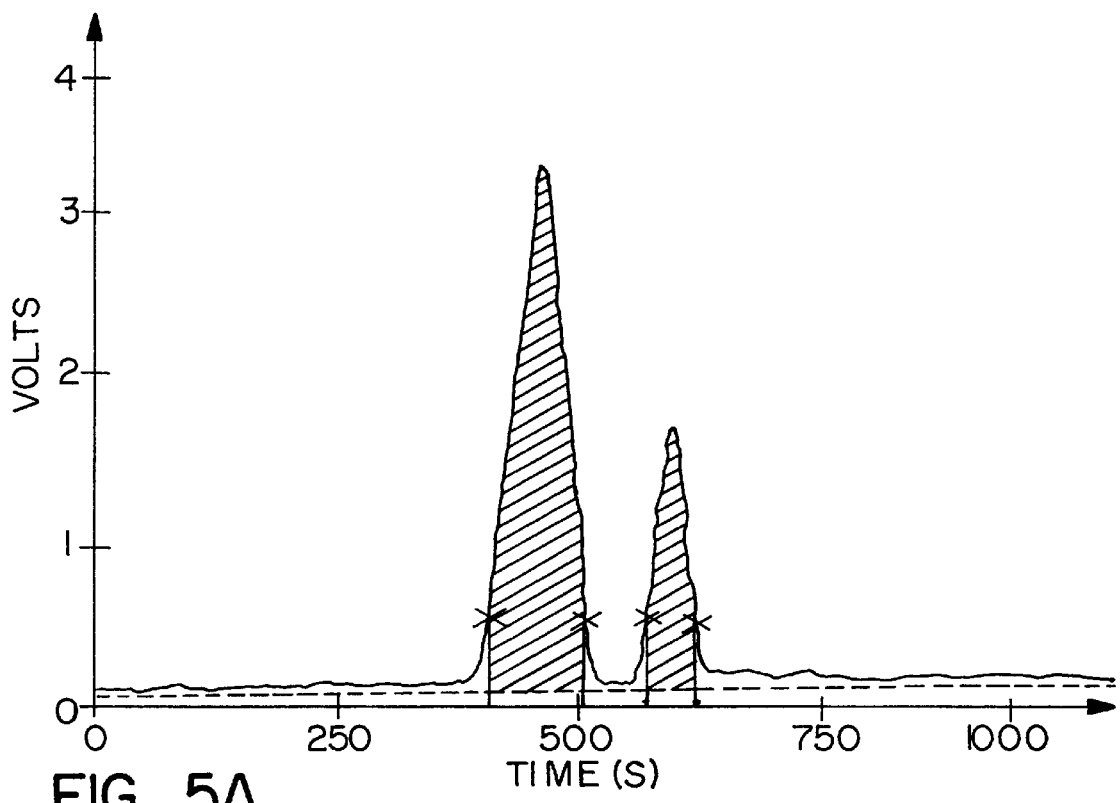
FIGS. 5A and 5B are exemplary electropherograms illustrating the process by which the automated capillary electrophoresis method and apparatus determines the area and width of acceptable peaks and skewed peaks, respectively.

Conventional capillary electrophoresis techniques would construct an electropherogram and subsequently analyze the electropherogram by means of a time intensive and labor intensive manual process. According to the present invention, however, the electropherogram need not even be displayed for the system operator. Instead, the data collected by the detector 20 over time from which the electropherogram would be constructed is automatically processed in order to determine the selected parameters. In this regard, the signal processor 22 includes peak identifying means 26 for automatically identifying the peaks within the data collected by the detector. In particular, the signal processor identifies those portions of the data which exceed a predetermined threshold as peaks. As such, the peak is bounded by a start point and an end point at which points the data collected by the detector crosses the predetermined threshold as designated by an "X" in FIG. 5A. In one advantageous embodiment, the signal processor determines the predetermined threshold based upon the absolute value of the maximum output voltage $V_{max}$ and the absolute value of the minimum output voltage $V_{min}$ measured by the detector during a run as follows: Peak Threshold=$[V_{max}-V_{min}]/20$. If desired, however, the peak threshold can set to a preselected value regardless of $V_{max}$ and $V_{min}$ or, alternatively, the peak threshold can be determined based upon other mathematical formulas.

The signal processor 22 also includes area determining means 28 for integrating each peak to determine the area under the respective peaks and the width of each respective peak. See block 56. Although the signal processor can determine the area under the respective peaks in a variety of manners, the signal processor of one advantageous embodiment determines the area under the respective peaks that is above a baseline and between the start point and the end point, i.e., the cross-hatched areas in FIG. 5A. The baseline can also be set in a varity of manners. According to one advantageous embodiment, however, the baseline is a line having a y-intercept equal to the maximum noise level and a slope that equals the average of the respective slopes of the lines connecting each pair of adjacent data points collected by the detector 20. As shown in dashed lines in FIGS. 5A and 5B, the baseline is therefore typically a generally horizontal line having little, if any, slope and a magnitude that approximates the maximum noise level. The signal processor of one advantageous embodiment also determines the maximum noise level based upon the absolute value of the maximum output voltage $V_{max}$ and the absolute value of the minimum output voltage $V_{min}$ measured by the detector during a run as follows: Maximum Noise Level=$[V_{max}-V_{min}]/100$. If desired, however, the maximum noise level can set to a preselected value regardless of $V_{max}$ and $V_{min}$ or, alternatively, the maximum noise level can be determined based upon other mathematical formulas.

Figure 5B:
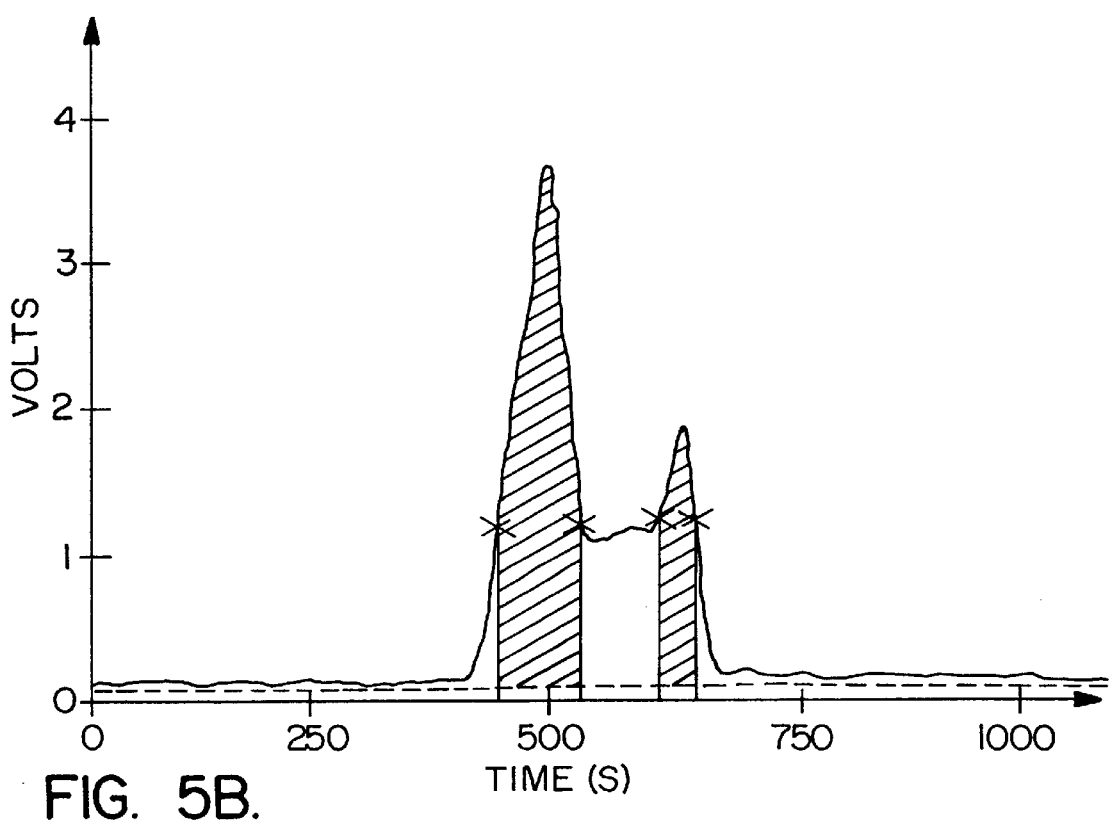

The signal processor 22 of one advantageous embodiment also includes peak analyzing means 34 for determining if the peaks are skewed or otherwise unacceptable. See block 58. While a skewed peak can be defined in a variety of manners, a peak is generally considered to be skewed if the peak does not rise and fall in a symmetrical manner, as illustrated by FIG. 5B. Moreover, a peak which is defined by a line having a slope which changes in sign two or more times, such as shown in FIG. 5B, is also typically considered skewed. Accordingly, the operator can visually determine if one or more peaks are skewed by reviewing the electropherograms. Alternatively, the peak analyzing means can automatically determine if a peak is skewed, such as by analyzing the data collected by the detector 20 to determine if the peak is assymetrical or to determine if the slope of the line that defines the peak changes sign two or more times between the start point and the end point of the peak.

As indicated by block 58, peaks which are not skewed can be otherwise unacceptable. For example, peaks which have a width, as measured between the start point and the end point, or peaks which define an area which exceeds a predetermined maximum value may be unacceptable since excessively broad peaks or excessively large peaks may not accurately represent the characteristics of the sample that is under investigation. Accordingly, the peak analyzing means 34 of the signal processor 22 can automatically identify those peaks having a width which exceeds a predetermined maximum width and/or an area which exceeds a predetermined maximum area as being potentially unacceptable.

The signal processor 22 could immediately determine that any peaks that are found to be skewed, excessively broad and/or excessively large are unacceptable. However, prior to identifying any peaks as unacceptable, the signal processor 22 of one advantageous embodiment first compares the peaks of the electropherogram generated for one of the runs that have been identified as potentially unacceptable with the corresponding peaks of the electropherograms generated for other runs. If the corresponding peaks generated during the other runs do not exhibit the same potentially unacceptable characteristics, i.e., the corresponding peaks are not skewed, excessively broad or excessively large, the signal processor will designate the peaks as unacceptable. If, however, the corresponding peaks generated during the other runs do exhibit the same characteristics, such as being skewed, excessively broad or excessively large, the signal processor of this advantageous embodiment will determine that the peaks are actually acceptable since the shape and size of the peak is repeatable or reproducible. In fact, since the shape and size of the peak is reproducible, the unique shape and size of the peak can be utilized to identify the presence and the concentration of the respective ion.

For example, it has been determined that the hydroxide ion ($OH^-$) typically generates a slightly skewed and slightly broad peak. See FIGS. 4C and 4E. Since the automated capillary electrophoresis method and apparatus 10 of the present invention repeatedly generates electropherograms which represent the hydroxide ion with the same uniquely shaped peak, the signal processor 22 will preferably determine that the peak is acceptable, even though the peak may be slightly skewed and somewhat broad.

If a peak is designated as being unacceptable, however, the signal processor 22 of one advantageous embodiment permits the operator to reset the peak threshold and/or the maximum noise level for the peak which has been determined to be unacceptable in an attempt to more accurately define the peak. See block 62. As shown in FIG. 5B, for example, the operator can individually reset the peak threshold for each of the adjacent peaks that have blended together, such as by separately raising the peak threshold for each peak as exemplified by the start and end points for each peak that are designated as "X" in FIG. 5B. Once the peak threshold and/or the maximum noise level have been reset, the area determining means 28 can reintegrate the peak to again determine the area under each peak and the width of each peak as shown in block 64. Thereafter, the peak analyzing means 34 of the signal processor can again determine if the peak, as defined by the reset peak threshold and/or the reset maximum noise level, is still skewed or otherwise unacceptable. See block 66. If the peak analyzing means continues to determine that the peak is unacceptable, another sample can be introduced to the sample reservoir 16 at the head end of the capillary 14 and the automated capillary electrophoresis method can be repeated. However, if the peak analyzing means determines that the peak, as defined by the reset peak threshold and/or the reset maximum noise level, is acceptable, such as by having the same general size and shape as the corresponding peak of the electropherograms generated by other runs, the run need not be repeated and the automated capillary electrophoresis method can proceed.

If the peaks were acceptable, either initially or following reintegration, the signal processor 22 then determines if the requested number of runs or iterations have been completed. See block 68. If the requested number of runs have not been completed, the capillary electrophoresis method is repeated for the sample in order to generate another electropherogram which is subsequently analyzed in the automated fashion described above.

If the predetermined number of runs have been completed, the automated capillary electrophoresis method and apparatus 10 and, more particularly, the signal processor 22 can separately determine the selected parameters based upon the results of each individual run. Thereafter, the signal processor can determine the average of each selected parameter as described in more detail below. For example, the average concentration of a respective ion within the sample can be determined by averaging the concentration of the respective ion determined for each run.

In order to provide a base line with which to compare the results, however, the automated capillary electrophoresis method and apparatus 10 of one advantageous embodiment not only analyzes the sample, but also analyzes a solution which contains both the sample and a standard ion solution. The standard ion solution includes predetermined concentrations of one or more of the ions within the sample. In this embodiment, the system operator initially enters the concentration of each ion of the standard ion solution (hereinafter "standard") as shown in block 70. The standard plus the sample is then introduced into the sample reservoir 16 at the head end of the capillary 14. See block 72. As described above, the system operator then enters a file name to identify and track the resulting data as shown in block 74.

The standard plus sample is then subjected to capillary electrophoresis by applying a voltage potential across the capillary 14 and by illuminating each zone of the sample plus standard as each zone advances through the capillary and past the detector 20 as shown in blocks 76 and 78. Based upon the light passing through each zone, the automated capillary electrophoresis method and apparatus 10 of one advantageous embodiment can determine the relative transparency of each discrete zone as shown in block 80. However, the automated capillary electrophoresis method and apparatus can measure other predetermined properties of each zone, as described above, without departing from the spirit and scope of the present invention. By constructing an electropherogram of the data collected by the detector over time and by integrating the peaks of the electropherogram so as to determine the area under each peak and the width of each peak, the automated capillary electrophoresis method and apparatus can analyze the standard plus sample as described above and as shown in blocks 82–94.

Once the requested number of runs or iterations with the standard plus sample have been completed as shown in block 96, the automated capillary electrophoresis method and apparatus 10 can determine the concentration of each ion within the sample. In this regard, the signal processor 22 preferably includes ion concentration determining means 30 which determines the concentration of each ion within the sample according to the following equation:

$$\frac{X_{ION}}{DF(X_{STD} + X_{ION})} = \frac{A_{ION}}{A_{STD+SAMPLE}} \quad (1)$$

wherein $X_{SAMPLE}$ is the concentration in parts per million (ppm) of the respective ion, $X_{STD}$ is the predetermined concentration of the respective ion in the standard solution, DF is the dilution factor of the solution containing the standard plus the sample, $A_{ION}$ is the area under the peak corresponding to the respective ion as determined from an analysis of the sample alone, and $A_{STD+SAMPLE}$ is the area under the peak corresponding to the respective ion as determined from an analysis of the solution containing the standard plus the sample. See block 98.

Based upon the concentration of the respective ions within the sample, the automated capillary electrophoresis method and apparatus 10 can automatically determine other selected sample parameters. In particular, the signal processor 22 can include parameter determining means 32 for automatically determining other selected sample parameters, such as the percent activity and percent sulfidity of the sample. See block 100. As described below, the percent activity and percent sulfidity are important measures of the liquor composition during the kraft paper process and will be described in more detail hereinbelow. In other applications, however, the signal processor can be configured to determine other sample parameters based upon the concentrations of the respective ions within the sample. Thereafter, the results, such as the concentrations of the respective ions or the other sample parameters, can be presented upon display 24 and a hard copy can be printed for further review, as shown in block 102.

The automated capillary electrophoresis method and apparatus 10 can advantageously monitor a wide variety of manufacturing processes which produce, consume or otherwise utilize various solutions. For example, the automated capillary electrophoresis method and apparatus can monitor the processes by which soft drink syrups, various chemicals and a wide variety of cleaning products are manufactured, to name but a few.

Figure 3:
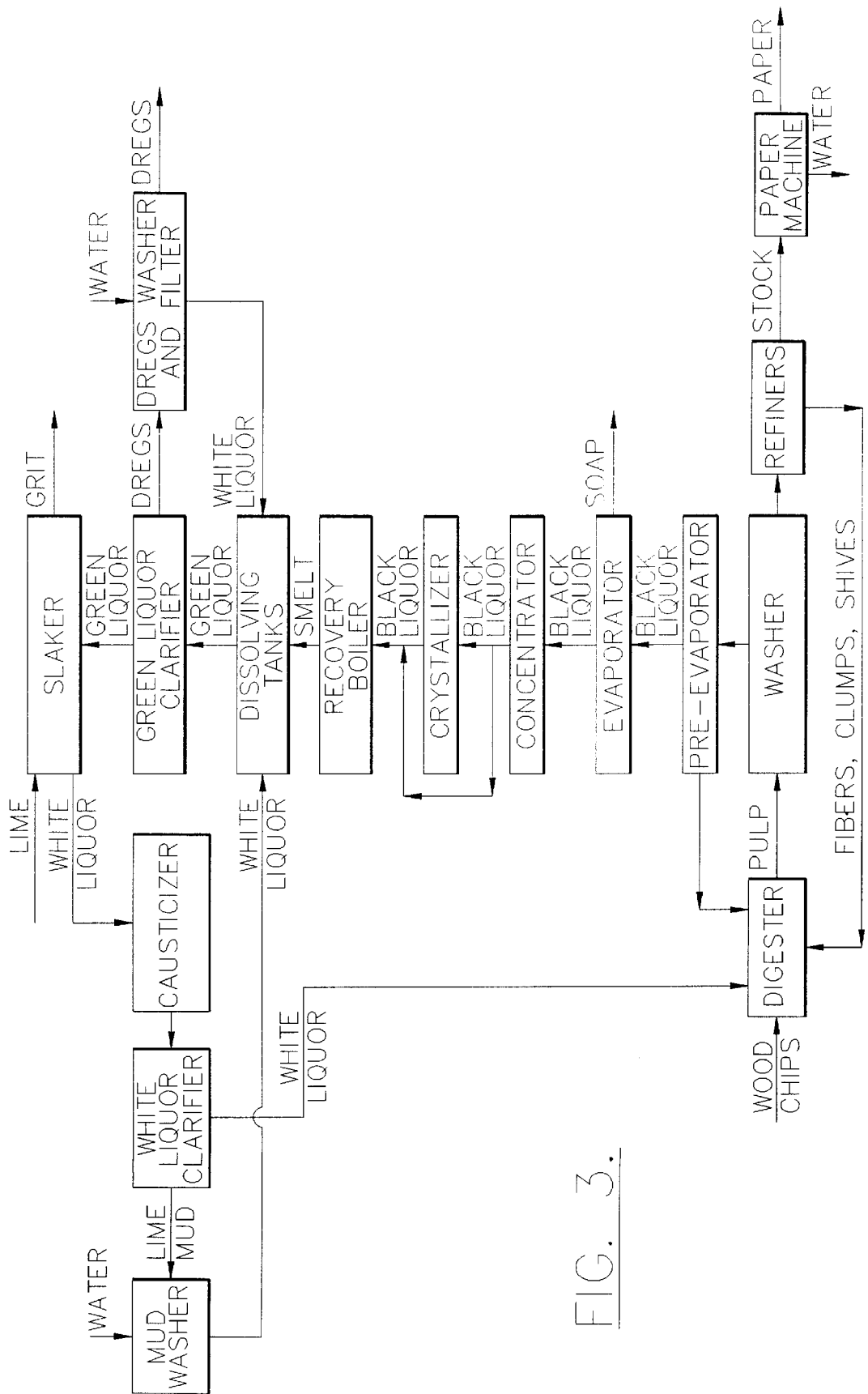
FIG. 3 is a block diagram illustrating the operations performed during a conventional kraft paper process.

As described above, one advantageous application of the automated capillary electrophoresis method and apparatus 10 is the kraft paper industry. A flow chart of the kraft paper process is shown in FIG. 3. A kraft paper process mixes inorganic chemicals with wood chips to separate lignin from the wood fibers. Typically, the lignin is removed by cooking wood chips within a digester in an aqueous solution of NaOH and white liquor. The spent liquor, i.e., black liquor, containing organic and inorganic ions is then concentrated and burned in a recovery boiler to obtain a smelt of $Na_2CO_3$ and $Na_2S$. The molten sodium salts are then dissolved in dissolving tanks to form green liquor which is reacted with lime to regenerate the white liquor in the slaker. The regenerated white liquor is then mixed with NaOH in the digester to again remove lignin from additional wood chips.

The composition of the white, black and green liquors during the kraft paper process will determine, in large part, the quality of the resulting pulp. The white, black and green liquors include different concentrations of chloride ions, thiosulfate ions, hydroxide ions, carbonate ions, sulfate ions, sulfite ions and sulfide ions. Thus, the automated capillary electrophoresis method and apparatus 10 of this embodiment is particularly tailored to identify the respective concentrations of these ions. In addition, the percent sulfidity and percent activity of the white liquor, black liquor and green liquor are other important parameters which provide additional information regarding the quality of the kraft paper process. In this regard, percent activity and percent sulfidity are defined as follows:

$$\% \text{ Activity} = \frac{NaOH + HS}{NaOH + HS + CO_3} \quad (2)$$

$$\% \text{ Sulfidity} = \frac{2(HS)}{NaOH + HS} \quad (3)$$

wherein NaOH, HS and $CO_3$ are the concentrations in ppm of the hydroxide, sulfate and carbonate ions, respectively.

In this embodiment, the electrolyte solution for analyzing white liquor preferably includes a 5 mM sodium chromate (analytical or reagent grade) solution that is 1.33% in CIA-PAK™ OFM anion BT in 18 MΩ deionized water. CIA-PAK™ OFM anion BT is available from Waters Chromatography Division of Millipore Corporation of Milford, Mass. This electrolyte solution is prepared by dissolving 0.0810 grams of sodium chromate in 90 mL of 18 MΩ deionized water and by thereafter adding 1.33 mL of CIA-PAK™ OFM anion BT. This solution is then diluted to 100 mL with 18 MΩ deionized water. Similarly, the buffer or electrolyte solution for analyzing the black and green liquors is preferably an 8 mM sodium chromate (analytical or reagent grade) solution that is 1.33% in CIA-PAK™ OFM anion BT in 18 MΩ deionized water. This electrolyte solution is preferably prepared by dissolving 0.1296 grams of sodium chromate in 90 mL of 18 MΩ deionized water and by thereafter by adding 1.33 mL of CIA-PAK™ OFM anion BT. This solution is also then diluted to 100 mL with 18 MΩ deionized water.

Prior to performing capillary electrophoresis upon the green liquor, black liquor and white liquor samples, the capillary 14 is preferably conditioned by pulling an NaOH conditioning solution through the capillary for 30 minutes with a vacuum pump. The NaOH conditioning solution is preferably prepared by dissolving a 0.12 gram pellet of sodium hydroxide (analytical or reagent grade) in 1.5 mL of 18 M• deionized water. Once the NaOH conditioning solution has been pulled through the capillary for approximately 30 minutes, the capillary is further conditioned by pulling the electrolyte or buffer solution which has been prepared for use with the particular type of liquor sample to be analyzed through the capillary for approximately five minutes with a vacuum pump. While the capillary need only be conditioned with the NaOH conditioning solution prior to the first run of the day, the capillary is preferably conditioned with the proper electrolyte or buffer solution between each run or iteration.

Following conditioning with the proper electrolyte solution, a liquor sample, such as a sample of white, black, or green liquor, can be analyzed. In this regard, the liquor sample is initially diluted. For example, white liquor is typically diluted by mixing one part white liquor with 213 parts deionized water, black liquor is typically diluted by mixing one part black liquor with 65.7 parts deionized water and green liquor is typically diluted by mixing one part liquor with 186.5 parts deionized water. By applying an electric potential across the capillary 14, the diluted liquor sample is drawn through the capillary. By detecting the light passing through the capillary over time, the automated capillary electrophoresis method and apparatus 10 can analyze the liquor as described above.

Once the predetermined number of runs have been made with the liquor sample, the automated capillary electrophoresis method and apparatus 10 of one advantageous embodiment preferably performs capillary electrophoresis, as described above, upon a solution containing both the liquor sample and a standard ion solution to establish a base line for comparison purposes. The standard ion solution is preferably prepared in advance. In particular, two standard ion solutions are preferably prepared for each type of liquor with one standard ion solution serving as a standard for the $OH^-$, $HS^-$, $CO_3^{2-}$ ions and the other standard ion solution serving as a standard for the $Cl^-$, $S_2O_3^{2-}$ and $SO_4^{2-}$ ions.

In one advantageous embodiment, the standard ion solution for the $Cl^-$, $S_2O_3^{2-}$, and $SO_4^{2-}$ ions for white, black and green liquors is prepared by initially determining the final volume $V_f$ of the dilute standard solution to make. Typically, $V_f$ is between about 50 mL and about 100 mL. However, $V_f$ can vary widely without departing from the spirit and scope of the present invention.

The volume $V_c$ of each concentrated certified standard ion solution of concentration $C_c$ which is required to provide a predetermined final concentration $C_f$ for each ion following dilution of the standard solution to final volume $V_f$ is determined for each ion as follows:

$$V_c = \frac{V_f C_f}{C_c} \quad (4)$$

In one advantageous embodiment, $C_f$ for $Cl^-$ ions is 200 ppm, $C_f$ for $S_2O_3^{2-}$ ions is 200 ppm and $C_f$ for $SO_4^{2-}$ ions is 200 ppm. The calculated volumes $V_c$ of each concentrated certified standard ion solution are then combined in a nalgene container and 18 MΩ deionized water is added to bring the total volume to the final volume $V_f$.

With respect to the standard ion solution for $OH^-$, $HS^-$ and $CO_3^{2-}$ ions, a different standard ion solution is preferably prepared for analyzing white, black and green liquors. As described above, however, the final volume $V_f$ of each standard ion solution is prepared by mixing the volumes $V_c$ of each concentrated certified standard ion solution, as calculated pursuant to equation 4, with 18 MΩ deionized water. With respect to the calculation of each concentrated certified standard ion solution pursuant to equation 4 for the standard ion solution for analyzing white liquor, $C_f$ for $OH^-$ ions is 700 ppm, $C_f$ for $HS^-$ ions is 350 ppm and $C_f$ for $CO_3^{2-}$ ions is 300 ppm. With respect to the standard ion solution for analyzing black liquor, $C_f$ for $OH^-$ ions is 600 ppm, $C_f$ for $HS^-$ ions is 200 ppm and $C_f$ for $CO_3^{2-}$ ions is 300 ppm. Likewise, with respect to the standard ion solution for analyzing green liquor, $C_f$ for $OH^-$ ions is 600 ppm, $C_f$ for $HS^-$ ions is 450 ppm and $C_f$ for $CO_3^{2-}$ ions is 1200 ppm.

In order to perform capillary electrophoresis upon the standard plus sample, the liquor sample is diluted with the appropriate standard ion solution which has been prepared as described above. Typically, the liquor sample and the standard ion solution are diluted one to one. Once the capillary 14 has been conditioned by pulling the proper electrolyte solution through the capillary for no more than two minutes, the automated capillary electrophoresis method and apparatus 10 performs capillary electrophoresis upon the solution containing both the sample and the standard ion solution. As described above, the capillary should be reconditioned between each run or iteration.

Figure 4C:
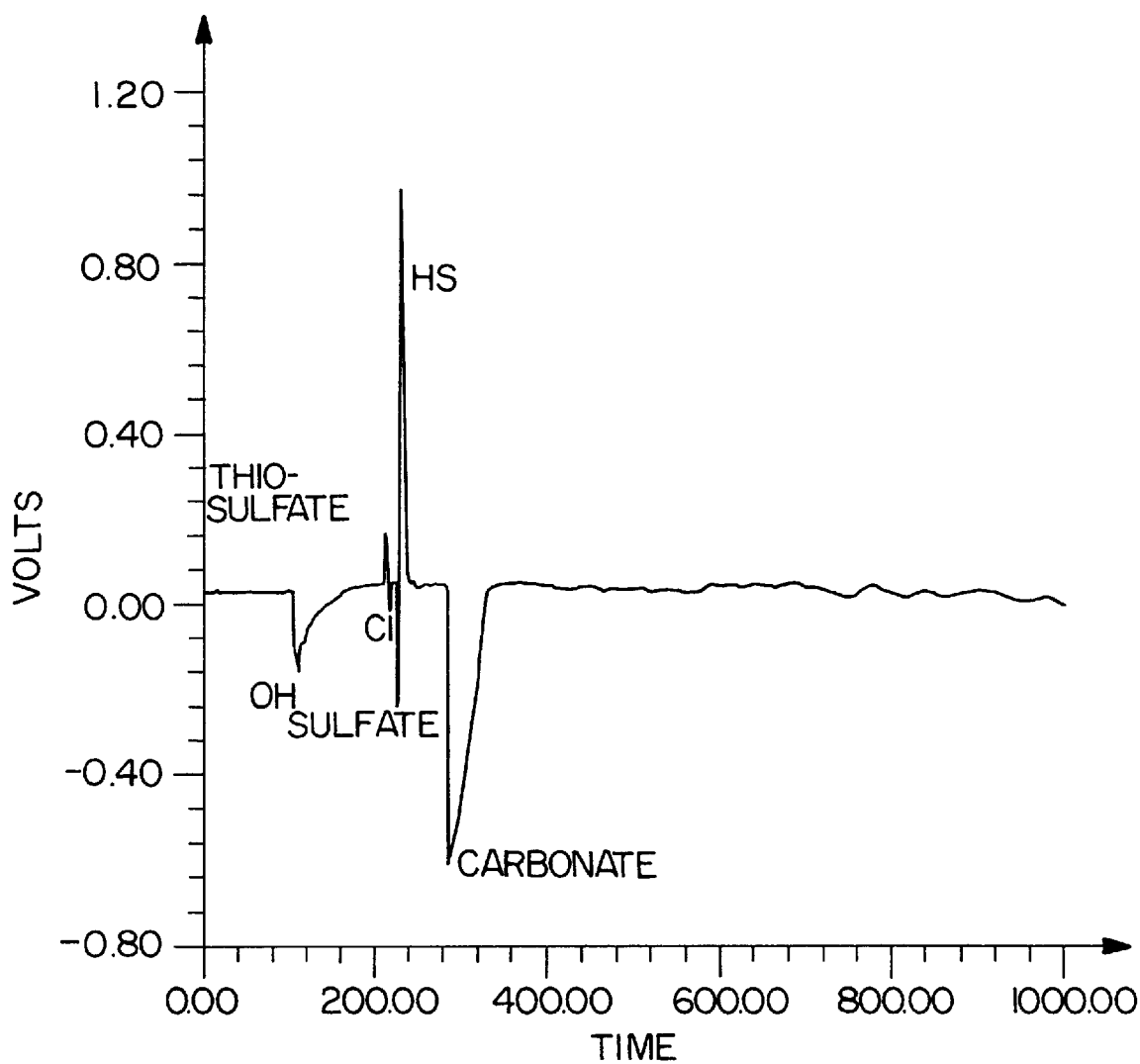
Figure 4D:
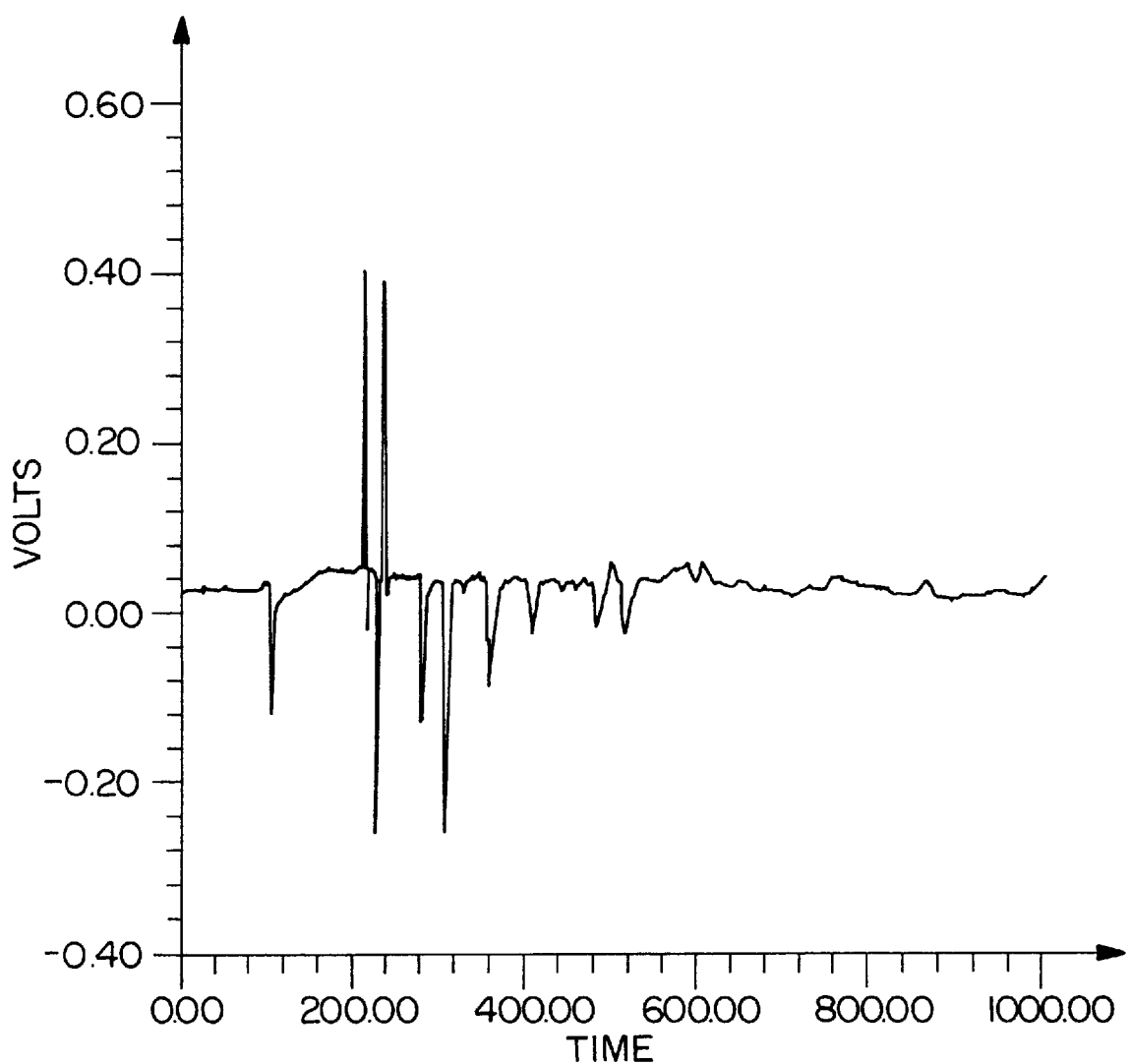
Figure 4E:
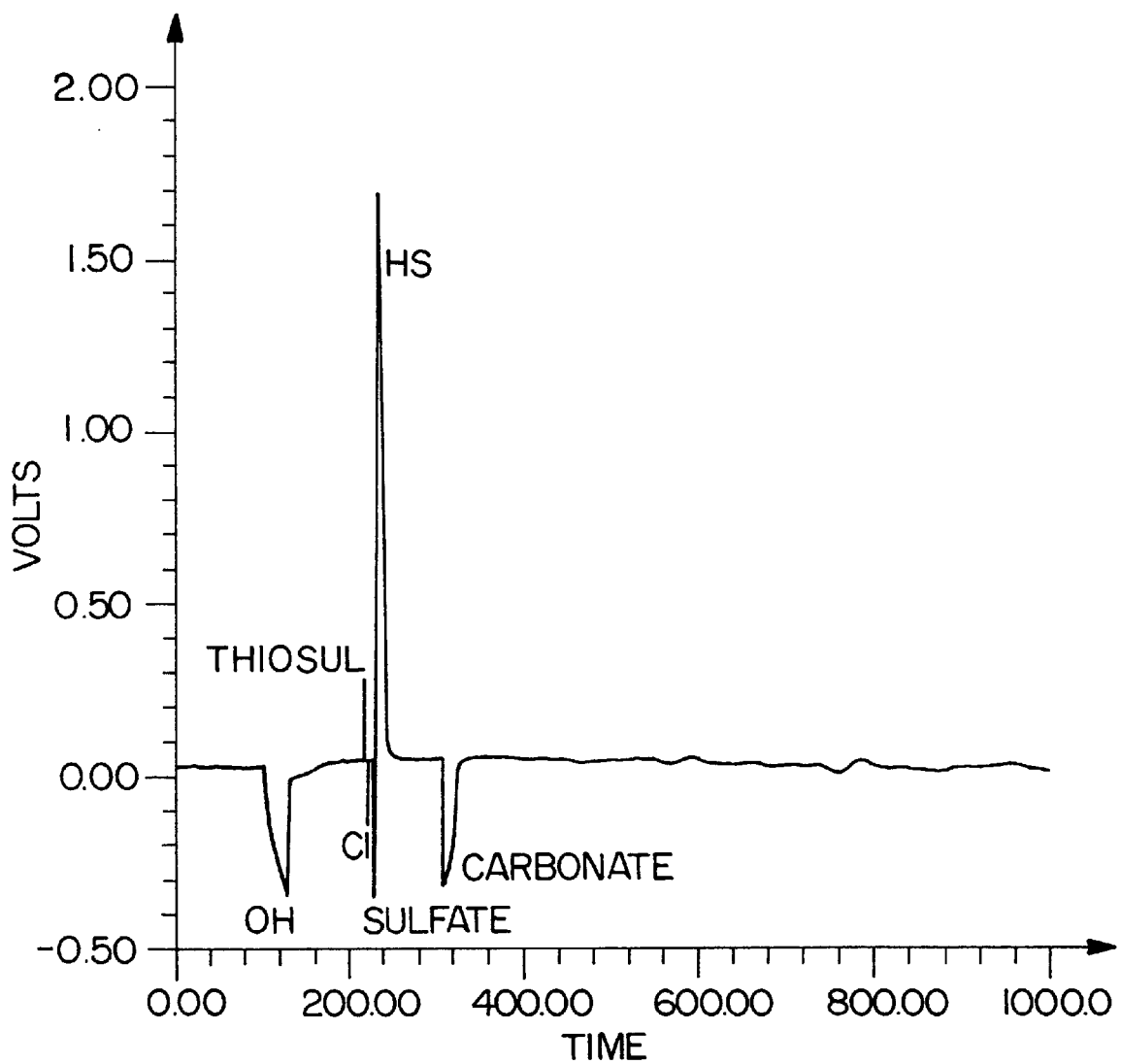

Following capillary electrophoresis of both the liquor sample and the standard plus sample, the automated capillary electrophoresis method and apparatus 10 can determine the concentrations of the respective ions in the liquor sample as well as other parameters of interest to the system operator, such as a percent activity and percent sulfidity of the liquor sample. In this regard, electropherograms constructed based upon data collected during capillary electrophoresis of green, black and white liquor samples are shown in FIGS. 4C–4E respectively. As indicated in FIGS. 4C–4E, the electropherograms include a peak for each respective ion within the liquor sample. By analyzing the area under each respective peak, the concentration of each ion can be automatically determined by the automated capillary electrophoresis method and apparatus in the manner described above.

This automated capillary electrophoresis analysis is preferably repeated so as to separately analyze each different type of liquor, i.e., white liquor, black liquor and green liquor. Following the automated capillary electrophoresis analysis of the white, black and green liquors, the system operator can determine if the respective ions are present in the proper concentrations within the white, black and green liquors. In this fashion, the automated capillary electrophoresis method and apparatus 10 of this embodiment can automatically determine if the kraft paper process is operating properly, i.e., within specifications, or improperly by identifying the concentrations of the respective ions of the white liquor, black liquor and/or green liquor and by determining the percent activity and percent sulfidity of each of these liquors.

By automatically identifying those liquor samples having a present activity and/or a percent sulfidity which falls outside of the acceptable boundaries, the automated capillary electrophoresis method and apparatus 10 can quickly notify the system operator of any potential problems with the kraft paper process. Since the automated capillary electrophoresis method and apparatus is automatically performed in a real time or near real time fashion, the automated capillary electrophoresis method and apparatus may be configured to analyze the kraft paper process online, thereby improving the efficiency of the kraft paper process by immediately detecting errors or other problems within the kraft paper process prior to producing a significant amount of paper which does not meet specifications.

Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A method for automatically monitoring liquor composition within a kraft process, the method comprising the steps of:

performing capillary electrophoresis upon a liquor sample containing at least one ion to obtain data over time which relates to a predetermined property of at least a portion of the liquor sample, wherein the liquor sample is selected from the group consisting of black liquor, green liquor and white liquor;

automatically identifying at least one peak within the data, said identifying step comprising determining those portions of the data which exceed a predetermined threshold and which form a respective peak;

separately determining an area under respective ones of the peaks;

automatically analyzing the peaks identified within the data to determine if a peak is unacceptable; and automatically determining a concentration of a respective ion based upon the area under the peak which corresponds to the respective ion and which is acceptable.

2. A method according to claim 1 wherein said step of automatically determining the concentration of a respective ion comprises automatically determining the concentration of a respective ion selected from the group consisting of chloride ions, thiosulfate ions, hydroxide ions, carbonate ions, sulfate ions, sulfite ions and sulfide ions.

3. A method according to claim 1 wherein the sample is at least partially defined by a plurality of parameters including percent activity and percent sulfidity, and wherein the method further comprises the steps of:

selecting at least one of the plurality of parameters; and automatically determining the selected parameter based upon the concentration of the respective ion.

4. A method according to claim 1 wherein the step of automatically analyzing the peaks comprises automatically analyzing the peaks identified within the data to determine if a peak is skewed.

5. A method according to claim 1 further comprising the steps of:

selecting a number of runs to be performed upon the liquor sample; and repeating said performing, identifying, area determining and concentration determining steps for each run; and wherein the step of automatically analyzing the peaks comprises:

automatically comparing corresponding peaks identified within the data obtained during at least two runs; and automatically determining if the data obtained during at least one of the runs is unacceptable based upon the comparison of the corresponding peaks identified within the data during at least two runs.

6. A method according to claim 1 further comprising the step of performing capillary electrophoresis upon a solution containing both the liquor sample and a standard to obtain additional data over time which relates to the predetermined property of at least a portion of the solution containing both the liquor sample and the standard.

7. A method according to claim 6 further comprising the steps of:

automatically identifying at least one peak within the additional data obtained during said step of performing capillary electrophoresis upon a solution containing both the liquor sample and the standard, said identifying step comprising determining those portions of the additional data which exceed a predetermined threshold and which form a respective peak; and separately determining an area under respective ones of the peaks identified within the additional data obtained during said step of performing capillary electrophoresis upon a solution containing both the liquor sample and the standard.

8. A method according to claim 7 wherein said step of automatically determining the concentration of a respective ion comprises automatically determining the concentration of a respective ion based upon the area under the peak corresponding to the respective ion which was identified within the data obtained during said step of performing capillary electrophoresis upon the liquor sample and based upon the area under the peak corresponding to the respective ion which was identified within the additional data obtained during said step of performing capillary electrophoresis upon a solution containing both the liquor sample and the standard.

9. An apparatus for automatically monitoring liquor composition within a kraft process, the apparatus comprising:

means for performing capillary electrophoresis upon a liquor sample containing at least one ion to obtain data over time which relates to a predetermined property of at least a portion of the liquor sample, wherein the liquor sample is selected from the group consisting of black liquor, green liquor and white liquor; and a signal processor, responsive to said means for performing capillary electrophoresis, for automatically processing the data to determine a concentration of a respective ion within the liquor sample, said signal processor comprising:

means for automatically identifying at least one peak within the data, said identifying means comprising means for determining those portions of the data which exceed a predetermined threshold and which form a respective peak;

means, responsive to said identifying means, for separately determining an area under respective ones of the peaks;

means, also responsive to said identifying means, for automatically analyzing the peaks identified within the data to determine if a peak is unacceptable; and means, responsive to said area determining means and said analyzing means, for automatically determining the concentration of the respective ion based upon the area under the peak which corresponds to the respective ion and which is acceptable.

10. An apparatus according to claim 9 wherein said signal processor comprises means for automatically determining the concentration of a respective ion selected from the group consisting of chloride ions, thiosulfate ions, hydroxide ions, carbonate ions, sulfate ions, sulfite ions and sulfide ions.

11. An apparatus according to claim 9 wherein the sample is at least partially defined by a plurality of parameters including percent activity and percent sulfidity, and wherein said signal processor further comprises:

means, responsive to operator actuation, for selecting at least one of the plurality of parameters; and means, responsive to said selecting means and said concentration determining means, for automatically determining the selected parameter based upon the concentration of the respective ion.

12. An apparatus according to claim 9 wherein said analyzing means comprises means for automatically analyzing the peaks identified within the data to determine if a peak is skewed.

13. An apparatus according to claim 9 wherein said means for performing capillary electrophoresis subjects the liquor sample to a predetermined number of runs, and wherein said analyzing means comprises:

means, responsive to said identifying means, for automatically comparing corresponding peaks identified within the data obtained during at least two runs; and means, responsive to said comparing means, for automatically determining if the data obtained during at least one of the runs is unacceptable.

14. An apparatus according to claim 9 further comprising means for performing capillary electrophoresis upon a solution containing both the liquor sample and a standard to obtain additional data over time which relates to the predetermined property of at least a portion of the solution containing both the liquor sample and the standard.

15. An apparatus according to claim 14 wherein said identifying means also identifies at least one peak within the additional data obtained by said means for performing capillary electrophoresis upon a solution containing both the liquor sample and the standard, said identifying means further comprising means for determining those portions of the additional data which exceed a predetermined threshold and which form a respective peak, and wherein said area determining means also determines an area under respective ones of the peaks identified within the additional data obtained by said means for performing capillary electrophoresis upon a solution containing both the liquor sample and the standard.

16. An apparatus according to claim 15 wherein said concentration determining means automatically determines the concentration of a respective ion based upon the area under the peak corresponding to the respective ion which was identified within the data obtained by said means for performing capillary electrophoresis upon the liquor sample and based upon the area under the peak corresponding to the respective ion which was identified within the additional data obtained by said means for performing capillary electrophoresis upon a solution containing both the liquor sample and the standard.

* * * * *